(12) United States Patent
Carvill et al.

(10) Patent No.: US 7,132,575 B2
(45) Date of Patent: Nov. 7, 2006

(54) PROCESS FOR THE SYNTHESIS OF BISPHENOL

(75) Inventors: Brian Carvill, Evansville, IN (US); Katherine Glasgow, Evansville, IN (US); Michael Roland, Evansville, IN (US)

(73) Assignee: General Electric Company, Schenectady, NY (US)

( * ) Notice: Subject to any disclaimer, the term of this patent is extended or adjusted under 35 U.S.C. 154(b) by 137 days.

(21) Appl. No.: 10/612,101

(22) Filed: Jul. 1, 2003

(65) Prior Publication Data

US 2005/0004406 A1    Jan. 6, 2005

(51) Int. Cl.
*C07C 39/12*    (2006.01)
*C07C 39/16*    (2006.01)

(52) U.S. Cl. ..................... 568/727; 568/728
(58) Field of Classification Search ............... 568/727, 568/728
See application file for complete search history.

(56) References Cited

U.S. PATENT DOCUMENTS

| | | | |
|---|---|---|---|
| 2,607,776 A | 8/1952 | Vinton | |
| 2,667,489 A | 1/1954 | Fincke | |
| 2,775,620 A | 12/1956 | Williamson | |
| 3,037,052 A | 5/1962 | Bortnick | |
| 3,049,568 A | 8/1962 | Apel et al. | |
| 3,153,001 A | 10/1964 | Apel et al. | |
| 3,172,916 A | 3/1965 | Wagner | |
| 3,198,847 A | 8/1965 | Lanning | |
| 3,242,219 A | 3/1966 | Farnham | |
| 3,367,979 A | 2/1968 | Harper et al. | |
| 3,394,089 A | 7/1968 | McNutt et al. | |
| 3,431,082 A | 3/1969 | Sellin | |
| 3,489,208 A | 1/1970 | Manteufel | |
| 3,535,879 A | 10/1970 | Kuntz | |
| 3,634,341 A | 1/1972 | Gammill et al. | |
| 3,651,080 A | 3/1972 | Doebel et al. | |
| 3,655,739 A | 4/1972 | Clasen | |
| 3,760,006 A | 9/1973 | Gammill et al. | |
| 4,036,974 A | 7/1977 | Walker et al. | |
| 4,045,379 A | 8/1977 | Kwantes et al. | |
| 4,051,079 A | 9/1977 | Melby | |
| 4,053,522 A | 10/1977 | McClure et al. | |
| 4,059,705 A | 11/1977 | Walker | |
| 4,122,048 A | 10/1978 | Buchwalder et al. | |
| 4,123,542 A | 10/1978 | Walker | |
| 4,126,618 A | 11/1978 | Winter et al. | |
| 4,177,350 A | 12/1979 | Zirngibl et al. | |
| 4,191,843 A | 3/1980 | Kwantes et al. | |
| 4,239,919 A | 12/1980 | Halrston | |
| 4,308,404 A | 12/1981 | Kwantes et al. | |
| 4,308,405 A | 12/1981 | Kwantes | |
| 4,315,023 A | 2/1982 | Partyka et al. | |
| 4,346,247 A | 8/1982 | Faler et al. | |
| 4,365,099 A | 12/1982 | Faler et al. | |
| 4,369,293 A | 1/1983 | Heydenreich et al. | |
| 4,391,997 A | 7/1983 | Mendiratta | |
| 4,396,728 A | 8/1983 | Faler | |
| 4,400,555 A * | 8/1983 | Mendiratta | 568/728 |
| 4,419,495 A | 12/1983 | Davis | |
| 4,423,252 A | 12/1983 | Maki et al. | |
| 4,424,283 A | 1/1984 | Faler et al. | |
| 4,478,956 A | 10/1984 | Maki et al. | |
| 4,496,667 A | 1/1985 | Reichgott et al. | |
| 4,535,084 A | 8/1985 | Lombardino et al. | |
| 4,549,900 A | 10/1985 | Kramer et al. | |
| 4,579,857 A | 4/1986 | Sherlock | |
| 4,579,862 A | 4/1986 | Manley et al. | |
| 4,584,383 A | 4/1986 | Parhi | |
| 4,584,416 A | 4/1986 | Pressman et al. | |
| 4,590,303 A | 5/1986 | Mendiratta | |
| 4,595,704 A | 6/1986 | Fazio | |
| 4,675,458 A | 6/1987 | Riemann et al. | |
| 4,753,947 A | 6/1988 | Dorn et al. | |
| 4,758,573 A | 7/1988 | Manley et al. | |
| 4,789,745 A | 12/1988 | Lin | |
| 4,820,740 A | 4/1989 | Li | |
| 4,822,923 A * | 4/1989 | Li | 568/724 |
| 4,825,010 A | 4/1989 | Li | |
| 4,847,432 A | 7/1989 | Faler | |
| 4,859,803 A * | 8/1989 | Shaw | 568/727 |
| 4,895,905 A | 1/1990 | Schneider | |
| 4,912,263 A | 3/1990 | Rudolph et al. | |
| 4,918,245 A | 4/1990 | Iimuro et al. | |
| 4,931,594 A | 6/1990 | Knebel et al. | |
| 5,021,521 A | 6/1991 | Krabbenhoft et al. | |
| 5,036,073 A | 7/1991 | Elbe et al. | |
| 5,073,575 A | 12/1991 | Blanch et al. | |
| 5,075,511 A | 12/1991 | Li | |
| 5,087,767 A | 2/1992 | Okamoto et al. | |
| 5,100,460 A | 3/1992 | Desbordes et al. | |

(Continued)

FOREIGN PATENT DOCUMENTS

EP    0 552 518    1/1992

(Continued)

OTHER PUBLICATIONS

JP11179210. Publication Date: Jul. 6, 1999. Ion Exchange Resin and Preparation of Bisphenols Using Same as Catalyst. Abstract Only.

(Continued)

*Primary Examiner*—Brian Davis (57) ABSTRACT

A process for the production of a bisphenol comprises reacting a feed comprising a phenol, a ketone and water in the presence of an ion exchange resin catalyst to produce an effluent; determining the para—para bisphenol selectivity of the reaction; and adjusting the concentration of the water in the feed based upon the para—para bisphenol selectivity in the effluent.

26 Claims, 2 Drawing Sheets

U.S. PATENT DOCUMENTS

| | | | |
|---|---|---|---|
| 5,141,966 A | 8/1992 | Porath | |
| 5,175,167 A | 12/1992 | Zipperer et al. | |
| 5,212,206 A | 5/1993 | Rudolph et al. | |
| 5,233,096 A | 8/1993 | Lundquist | |
| 5,284,981 A | 2/1994 | Rudolph et al. | |
| 5,296,609 A | 3/1994 | McCort et al. | |
| 5,302,774 A * | 4/1994 | Berg et al. | 568/727 |
| 5,304,688 A | 4/1994 | Bowman et al. | |
| 5,315,042 A | 5/1994 | Cipullo et al. | |
| 5,395,857 A | 3/1995 | Berg et al. | |
| 5,414,151 A | 5/1995 | Pressman et al. | |
| 5,414,152 A | 5/1995 | Cipullo | |
| 5,428,075 A | 6/1995 | Pressman et al. | |
| 5,436,344 A | 7/1995 | Quallich | |
| 5,455,282 A | 10/1995 | Berg et al. | |
| 5,463,140 A | 10/1995 | Wehmeyer et al. | |
| 5,475,154 A | 12/1995 | Lundquist et al. | |
| 5,545,764 A | 8/1996 | Berg et al. | |
| 5,589,517 A | 12/1996 | Sugawara et al. | |
| 5,608,071 A | 3/1997 | Quallich | |
| 5,629,456 A | 5/1997 | Yamada et al. | |
| 5,631,338 A | 5/1997 | Inoue et al. | |
| 5,648,561 A | 7/1997 | Tan et al. | |
| 5,679,312 A | 10/1997 | Jin et al. | |
| 5,698,600 A | 12/1997 | Wulff et al. | |
| 5,700,943 A | 12/1997 | Daines | |
| 5,723,689 A | 3/1998 | Pressman et al. | |
| 5,723,691 A | 3/1998 | Cipullo et al. | |
| 5,756,781 A | 5/1998 | Sybert et al. | |
| 5,759,942 A | 6/1998 | Tan et al. | |
| 5,777,180 A | 7/1998 | June et al. | |
| 5,783,733 A | 7/1998 | Kissinger | |
| 5,785,823 A | 7/1998 | Meurer et al. | |
| 5,932,731 A | 8/1999 | Goda et al. | |
| 6,229,037 B1 | 5/2001 | Okubo et al. | |
| 6,288,284 B1 * | 9/2001 | Eek et al. | 568/728 |
| 6,414,200 B1 | 7/2002 | Spivack et al. | |
| 6,534,686 B1 | 3/2003 | Webb et al. | |
| 6,620,939 B1 | 9/2003 | Webb et al. | |
| 2003/0088130 A1 | 5/2003 | Webb et al. | |
| 2003/0153792 A1 | 8/2003 | Iwahara et al. | |
| 2004/0019241 A1 | 1/2004 | Chiang et al. | |
| 2004/0030196 A1 | 2/2004 | Saruwatari et al. | |

FOREIGN PATENT DOCUMENTS

| | | |
|---|---|---|
| EP | 0 856 505 | 1/1998 |
| EP | 1 371 623 A1 | 2/2002 |
| FR | 2 317 264 | 4/1977 |
| GB | 1185223 | 3/1970 |
| JP | 57031629 A * | 2/1982 |
| JP | 10021257 A * | 1/1998 |
| JP | 10251180 A * | 9/1998 |
| WO | WO 97/08122 | 3/1997 |
| WO | WO 00/23408 | 4/2000 |
| WO | WO 00/50372 | 8/2000 |
| WO | WO 00/61532 | 10/2000 |
| WO | WO 01/74488 | 3/2001 |
| WO | WO 01/74489 | 3/2001 |
| WO | WO 01/49640 | 7/2001 |
| WO | WO 01/74750 | 10/2001 |
| WO | WO 02/070443 | 9/2002 |
| WO | WO 02/072516 | 9/2002 |
| WO | WO 02/085830 | 10/2002 |
| WO | WO 03/014049 | 2/2003 |
| WO | WO 03/055601 A1 | 7/2003 |
| WO | WO 2004/013075 A1 | 2/2004 |

OTHER PUBLICATIONS

JP57035533 Publication Date Feb. 26, 1982 "Preparation of Bisphenol" (Abstract Only).

FR 2 317 264 Publication Date Apr. 2, 1977. Translation.

International Search Report Dated Nov. 22, 2004.

JP2001054034. Publication Date Feb. 23, 2001. Abstract Only (1 page).

JP2001118012. Publication Date Apr. 27, 2001. Abstract Only (1 page).

FR 2685221. Publication No. Jun. 25, 1993. Abstract Only (1 page).

FR 2685323. Publication No. Jun. 25, 1993. Abstract Only (1 page).

DE 3619450. Publication Date Dec. 16, 1987. Abstract Only (1 page).

EP 0676237. Publication Date Oct. 11, 1995. Abstracr Only (1 page).

EP1160229. Publication Date Dec. 5, 2001. Abstract Only (1 page).

EP 0788839. Publication Date Aug. 13, 1997. Abstract Only (1 page).

EP 0620041. Publication Date Oct. 19, 1994. Abstract Only (1 page).

JP 2000143565. Publication Date May 23, 2000. Abstract Only (1 page).

JP 2000281608. Publication Date Oct. 10, 2000. Abstract and Claims (6 pages).

JP 11255748. Publication Date Sep. 21, 1999. Abstract Only (1 page).

JP 2001317768. Publication Date Nov. 16, 2001. Abstract Only (1 page).

JP 2001021604. Publication Date Jan. 26, 2001. Abstract Only (1 page).

JP 2001054034. Publication Date Feb. 23, 2001. Abstract Only (1 page).

JP 2001056471. Publication Date Feb. 27, 2001. Abstract Only (1 page).

JP 2001064669. Publication Date Mar. 13, 2001. Abstract Only (1 page).

JP 2001060201. Publication Date Mar. 6, 2001. Abstract Only (1 page).

JP 2001064671. Publication Date Dec. 17, 2002. Abstract Only (1 page).

JP 05-294875. Publication Date Sep. 11, 1993. Abstract and Claims (5 pages).

JP 10-218814. Publication Date Aug. 18, 1998. Abstract and Claims (6 pages).

JP 11-246458. Publication Date Sep. 14, 1999. Abstract Only (3 pages).

JP 99179210. Machine Translation (1999) (13 pages).

JP 99255748. Machine Translation (1999) (9 pages).

JP 2002226417. Publication Date Aug. 14, 2002. Abstract Only (1 page).

JP 2001-286770. Publication Date Oct. 16, 2001. Abstract and Claims (5 pages).

JP 08-071433. Publication Date Mar. 19, 1996. Abstract and Claims (5 pages).

JP 10314595. Publication Date Dec. 2, 1998. Abstract and Claims (2 pages).

JP 10328573. Publication Date Dec. 15, 1998. Abstract anc Claims (2 pages).

JP 10211434. Publication Date Aug. 11, 1998. Abstract and Claims (2 pages).

JP 5271132. Publication Date Oct. 19, 1993. Abstractr and Claims (8 pages).

JP 8325185. Publication Date Dec. 10, 1996. Abstract and Claims (6 pages).

JP 11124351. Publication Date May 11, 1999. Abstract and Claims (9 pages).

JP 8038910. Publication Date Feb. 13, 1996. Abstract and Claims (5 pages).

JP 5294876. Publication Date Nov. 9, 1993. Abstract and Claims (4 pages).

* cited by examiner

FIG. 1

Catalyst deactivation

FIG. 2 p,p-BPA production-70 deg C

FIG. 3

Contour plot of conv

Hold values: Temp: 60.0

Contour plot of selectiv

Hold values: Temp: 60.0

——— 96.7
—··— 96.8
- - - - 96.9
· · · · · · 97.0
– – – 97.1
- - - - 97.2

PROCESS FOR THE SYNTHESIS OF BISPHENOL

BACKGROUND OF INVENTION

This disclosure relates to methods of making bisphenol employing an acidic ion exchange resin. In particular, this disclosure relates to methods of making bisphenol employing water addition to the reactants.

Typical bisphenols, such as 4,4'-isopropylidenediphenol, e.g., bisphenol-A (BPA), are widely employed as monomers in the manufacture of polymeric materials, such as engineering thermoplastics. For example, BPA is a principal monomer used in the manufacture of polycarbonate. Bisphenols are generally prepared by the electrophilic addition of aldehydes or ketones such as acetone to aromatic hydroxy compounds such as phenol, in the presence of an acidic catalyst composition. These types of reactions are also referred to as acid catalyzed condensation reactions. While commercially sulfonated polystyrene resin cross-linked with divinylbenzene, (PS-DVB) is typically used as the solid acid component of the catalyst composition, other acidic catalysts are also known to be effective in bisphenol synthesis. Zeolites, metal oxides, polysiloxanes, and other acid catalysts on organic and inorganic supports have been described as effective bisphenol catalysts. Reaction promoters can also be employed as part of the catalyst composition to improve the reaction rate, and selectivity, of the desired condensation reaction; in the case of BPA, the desired selectivity is for the para—para isomer. Promoters can be present as unattached molecules in the bulk reaction matrix, e.g., "bulk-promoters", or can be attached to the resin through ionic or covalent linkages, e.g., "attached-promoters". A useful class of promoter is the mercaptans, specifically thiols, e.g., organosulfur compounds which are derivatives of hydrogen sulfide.

Most catalysts that are used to produce bisphenols not only catalyze the desired condensation reaction to form bisphenol, but also catalyze isomerization reactions between bisphenol and other byproducts. While it is desirable to contact the reactants with the catalyst for sufficient time to maximize the production of bisphenol, one must also be careful not to have contact times be so large that the conversion of bisphenol to undesired products predominates. In other words, there is an optimum contact time, leading to an optimum concentration of bisphenol. In a continuous reactor, the contact time is the residence time in the reactor. Alternatively, the inverse of the residence time, known as the weight hourly space velocity (WHSV) can be used, where WHSV is defined as the weight of flow through the reactor bed per the weight of the catalyst per hour. It is normally desired to maximize the conversion to bisphenol (i.e., maximize selectivity) in order to minimize the amount of raw materials required to produce a unit of bisphenol.

Another complicating factor can be that the catalyst activity declines with time. This is a well known effect with acidic catalysts used in the manufacture of bisphenol. Since the catalyst activity declines, the effective contact time decreases (or the effective WHSV increases during the lifetime of the catalyst). Typically, in a commercial reactor, sufficient catalyst is loaded into the reactor to allow for a given production rate at the end of the catalyst life. However, the initial activity of the catalyst is high, and can lead to high conversions of reactants to bisphenol, and because of the series nature of the reaction, can also lead to isomerization of bisphenol to undesired by-products. In other words, the initial selectivity of the reaction can be lower than desired.

In addition to the problem discussed above, there are often circumstances in a chemical plant where it is necessary to adjust the reactors to produce less than the maximum amount of bisphenol. Since the amount of catalyst in the reactor is fixed, and reducing production requires the flow rate through the reactor to be decreased, the net effect is to decrease the WHSV, and to increase the residence time or the contact time. According to the discussion above, this increase in contact time can lead to more of the bisphenol being converted to by-products.

Accordingly, there is a need for a method to maintain selectivity over a range of flow rates and catalyst activities.

SUMMARY OF INVENTION

The above-described and other drawbacks and disadvantages of the prior art are alleviated by a process for the reaction of a ketone with a phenol to form a bisphenol comprising reacting a feed comprising a phenol, a ketone and water in the presence of an ion exchange resin catalyst to produce an effluent; determining the para—para bisphenol selectivity of the reaction; and adjusting the concentration of the water in the feed based upon the para—para bisphenol selectivity.

In another embodiment, a process for the manufacture of polycarbonate comprises reacting a feed comprising a phenol, a ketone and water in the presence of an ion exchange resin catalyst to produce an effluent comprising bisphenol; determining the para—para bisphenol selectivity of the reaction; adjusting the concentration of the water in the feed based upon the para—para bisphenol selectivity; and reacting said bisphenol with a carbonic acid derivative or a carbonate diester in the presence of a polymerization catalyst.

In another embodiment, a process for the reaction of a ketone with a phenol to form a bisphenol in the presence of a catalyst comprises determining the catalytic activity of the catalyst over time; introducing a feed comprising water; phenol and ketone to the catalyst; reacting the phenol and ketone in the presence of the catalyst; controlling the concentration of the water in the feed based upon the amount of catalyst and catalytic activity; wherein the reaction has a para—para bisphenol selectivity of at least about 94%.

In another embodiment, a process for the manufacture of polycarbonate comprises synthesizing a bisphenol in the presence of a catalyst by determining the catalytic activity of the catalyst; introducing a feed comprising water, phenol and ketone to the catalyst; reacting the phenol and ketone in the presence of the catalyst to form bisphenol; controlling the concentration of the water in the feed based upon the amount of catalyst and catalytic activity; and reacting the bisphenol with a carbonic acid derivative or a carbonic diester in the presence of a polymerization catalyst, wherein the reaction generating bisphenol has a para—para bisphenol selectivity of at least about 94%.

In another embodiment, a process for the reaction of a ketone with a phenol to form a bisphenol comprises reacting a feed comprising a phenol, a ketone and a first concentration of water in the presence of an ion exchange resin catalyst at a first flow rate to produce an effluent; and reacting a feed comprising a phenol, a ketone and a second concentration of water in the presence of the ion exchange resin catalyst at a second flow rate to produce an effluent, wherein the reaction at the first flow rate has a para—para bisphenol selectivity within about 1% of the para—para bisphenol selectivity of the reaction at the second flow rate and the first concentration of water does not equal the second concentration of water.

DETAILED DESCRIPTION

Bisphenol is produced by reacting a mixture of a phenol and a ketone in the presence of an acid catalyst. A packed bed reactor filled with an acidic ion exchange resin serves as the reaction vessel. A feed comprising ketone, water and excess phenol enters the top of the bed, the ketone is substantially consumed in the reaction, and bisphenol and water exit from the bottom of the reactor. Substantially consumed is herein defined as at least about 70% consumed, preferably at least about 90% consumed, based upon the weight of the ketone in the feed. Preferably the catalyst is selective for the production of a single isomer, typically para—para bisphenol (p,p-bisphenol). The rate at which reactants pass through the catalyst bed is defined as weight hour space velocity (WHSV), which is defined as the mass flow rate into the reactor (units of mass per hour) divided by the mass of the catalyst in the reactor. A newly charged catalyst is typically very active, consuming nearly all of the ketone well short of the bottom of the catalyst bed. In this situation, the remaining part of the catalyst bed acts may act as an isomerization catalyst, isomerizing some p,p-bisphenol to its undesired isomer, ortho-para bisphenol (o,p-bisphenol), thereby reducing the selectivity the reaction and the purity of the reactor effluent.

It has been discovered that water added at the beginning of a catalyst's lifetime will suppress isomerization reactions and will increase p,p-bisphenol selectivity and therefore p,p-bisphenol purity. As the catalyst deactivates, or the flow rate is modified, adjusting the amount of added water ensures a stable reaction selectivity and reactor effluent composition throughout the catalyst lifetime and over a range of flow rates. Without being bound by theory it is believed that the effect of the inclusion of water is to decrease the rate at which the catalyst converts the reactants to the desired product, providing a tool to obtain the optimum selectivity from the exit of the catalyst bed at a variety of catalyst activities and/or reactor flow rates. In addition, the process for bisphenol production described herein increases the average catalyst selectivity and maintains a more stable selectivity and reactor output throughout the catalyst life. Because more catalyst can be loaded into the reactor at the beginning of life with no impact on the selectivity, this can lead to longer times between catalyst change-outs. Thus the addition of water can be used as a mechanism to reduce the frequency of catalyst changeouts.

Water addition can be used to minimize the impact on selectivity when the flow rate through the reactor is decreased. This can occur when less production of bisphenol is desired. Because the amount of catalyst is fixed, a decrease in flow rate causes increased contact time, or decreased WHSV. This allows more time for the bisphenol that is formed to be converted (via isomerization) to undesired products. During these times, the amount of water added to the reactor influent is increased to obtain the optimum BPA selectivity.

The bisphenol production process has high selectivity for para—para (p/p)bisphenol and a high conversion level, thereby significantly reducing the complexity of the large scale isolation processes required to obtain the isolated bisphenol. Additionally, the selectivity for p,p bisphenol is substantially constant over the useful lifetime of the catalyst, resulting in a more stable and consistent process. The p/p selectivity of the reaction is greater than or equal to about 94%, preferably greater than or equal to about 95%, and more preferably greater than or equal to about 96%. P/p selectivity of the reaction is determined by 100× (amount of p/p bisphenol created in the reactor/total amount of products created in the reactor).

The bisphenol production process typically exhibits conversion levels greater than or equal to about 70%, preferably greater than or equal to about 80% and more preferably greater than or equal to about 90%. As readily appreciated by one of ordinary skill in the art, conversion usually decreases over the lifetime of the catalyst. However, by employing water in the feed to the catalyst and varying the amount of water in the feed based on catalyst activity it is possible to maintain the conversion levels within about 70% to about 90% of the desired conversion level. It is contemplated that when the conversion level of the catalyst has decreased to less than about 70% and/or the feed contains less than about 0.05% water, the catalyst will be replaced or reactivated using methods known in the art such as those found in U.S. Pat. Nos. 5,428,075 and 5,455,282. Conversion is defined herein as 100×((ketone into reaction−ketone out of reaction)/ketone into reaction). Conversion has a theoretical maximum of 100%.

The high p/p selectivity and consistent conversion level of the continuous process is dramatic and unexpected. The effectiveness of a catalyst, as determined by selectivity and conversion, can vary dramatically based on reaction conditions and it is counter intuitive that the addition of a product of the reaction, namely water, to the reactants would increase selectivity. High catalyst selectivity in the reactor is desired in order to simplify downstream separation operations and to maximize raw material yields.

In another aspect, the process described herein demonstrates a total bisphenol reaction selectivity (para—para (p/p) and ortho-para (o/p) combined) of greater than or equal to about 94%. Additionally, the average p/p:o/p ratio of the materials generated by the reaction is greater than or equal to about 20, preferably greater than or equal to about 30 and more preferably greater than or equal to about 40. The high overall selectivity when combined with the high p/p:o/p ratio indicates that little or no impurity aside from o/p bisphenol is produced. It is also contemplated that the high overall reaction selectivity increases the life of the catalyst.

Phenol starting materials are aromatic hydroxy compounds which have at least one unsubstituted position, and optionally have one or more inert substituents such as hydrocarbyl or halogen at one or more ring positions. An inert substituent is a substituent which does not interfere undesirably with the condensation of the phenol and ketone or aldehyde and which is not, itself, catalytic. Preferably, the phenols are unsubstituted in the position para to the hydroxyl group.

Alkylene, alkyl, cycloaliphatic, aryl, arylene, alkylarylene, arylalkylene, alkylcycloaliphatic and alkylenecycloaliphatic are hydrocarbyl functions, that is, functions containing carbon and hydrogen atoms. The alkylene functions can be straight or branched chain and saturated and unsaturated, that is alkylene, alkenylene, or alkynylene. Cycloaliphatic hydrocarbon residues include both saturated and unsaturated cyclic residues, that is, cycloalkylene and cycloalkenylene. Arylene includes mono- and polycyclic aromatic residues, e.g. those of benzene, biphenyl, biaryl, naphthyl, phenanthrenyl, anthracenyl or aryl groups, including those bridged by an alkylene group. Alkaryl residues include alkyl, alkenyl and alkynyl-substituted aromatic rings. Aralkyl includes alkyl, alkenyl or alkynyl residues, substituted by one or more aromatic groups.

Alkyl groups include both straight- and branched-chain isomers of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, nonadecyl and eicosyl groups, as well as the corresponding unsaturated (alkenyl or alkynyl) groups, as well as higher homologues. Preferably, the alkyl groups are of 1–20 carbon atoms, more preferably of 1–5 carbon atoms, most preferably those of 1–3 carbon atoms. Alkyl of 1–5 carbon atoms includes the various methyl, ethyl, propyl, butyl and pentyl isomers. Alkyl, aryl, alkaryl and aralkyl substituents are suitable hydrocarbyl substituents on the phenol reactant.

Other inert substituents on the phenols include, but are not limited to alkoxy, aryloxy or alkaryloxy, wherein alkoxy includes methoxy, ethoxy, propyloxy, butoxy, pentoxy, hexoxy, heptoxy, octyloxy, nonyloxy, decyloxy and polyoxyethylene, as well as higher homologues; aryloxy, phenoxy, biphenoxy, naphthyloxy, etc. and alkaryloxy includes alkyl, alkenyl and alkylnyl-substituted phenolics. Additional inert substituents on phenols include halo, such as bromo, chloro or iodo.

Cyano and nitro substituents may deactivate the phenols and aldehyde and carboxylic acid substituents may cause interfering reactions. Additional hydroxyl substituents may be suitable in some cases.

Preferred substituents include alkyl moieties containing from 1 to about 10 carbon atoms, more preferably, lower alkyl moieties, containing from 1 to about 5 carbon atoms, most preferably from 1 to 3 carbon atoms. The alkyl substituents may be straight or branched chain isomers.

Exemplary phenols include, but are not limited to, phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tertbutylphenol, 2-phenylphenol, 1-naphthol, 2-naphthol and the like. Preferred phenols include phenol, 2- or 3-cresol, 2,6-dimethylphenol, resorcinol, naphthols, and mixtures thereof. Most preferably, the phenol is unsubstituted.

The phenol starting materials may be commercial grade or better. As readily understood by one of ordinary skill in the art commercial grade reagents may contain measurable levels of typical impurities such as acetone, α-methylstyrene, acetophenone, alkyl benzenes, cumene, cresols, water, hydroxyacetone, methyl benzofuran, methyl cyclopentenone, and mesityl oxide, among others.

The ketones, which are advantageously used, include any ketone having a single carbonyl (C═O) group or several carbonyl groups, and which are reactive under the conditions used. The ketones can be substituted with substituents that are inert under the conditions used. Inert substituents are as set forth above for the reactive phenols.

The ketones are advantageously selected from aliphatic, aromatic, alicyclic or mixed aromatic-aliphatic ketones, diketones or polyketones, of which acetone, methyl ethyl ketone, diethyl ketone, benzyl, acetyl acetone, methyl isopropyl ketone, methyl isobutyl ketone, acetophenone, ethyl phenyl ketone, cyclohexanone, cyclopentanone, benzophenone, fluorenone, indanone, 3,3,5-trimethylcyclohexanone, anthraquinone, 4-hydroxyacetophenone, acenaphthenequinone, quinone, benzoylacetone and diacetyl are representative examples.

Ketones having halo, nitrile or nitro substituents can also be used, for example, 1,3-dichloroacetone or hexafluoroacetone.

Aliphatic ketones which are useful starting materials include, but are not limited to acetone, ethyl methyl ketone, isobutyl methyl ketone, 1,3-dichloroacetone, hexafluoroacetone and the like. A preferred aliphatic ketone is acetone, which condenses with phenol to produce 2,2-bis-(4-hydroxyphenyl)-propane, commonly known as bisphenol A. Another preferred aliphatic ketone is hexafluoroacetone, which reacts with two moles of phenol to produce 2,2-bis-(4-hydroxyphenyl)-hexafluoropropane (bisphenol AF).

A preferred class of ketones has at least one hydrocarbyl group containing an aryl group, for example, a phenyl, tolyl, naphthyl, xylyl or 4-hydroxyphenyl group.

Other preferred ketones include those in which the hydrocarbon radicals connected to the carbonyl groups of the ketone is in a cycloaliphatic group. Examples of specific preferred ketones include 9-fluorenone, cyclohexanone, 3,3,5-trimethylcyclohexanone, indanone, indenone, anthraquinone and the like.

Most preferred ketones include 9-fluorenone, benzophenone, acetone, acetophenone, 4-hydroxyacetophenone, 4,4'-dihydroxybenzophenone and mixtures of the foregoing ketones. Most preferably, the process of this invention is used to make bisphenol A by reaction of phenol with acetone or to make 9,9-bis-(4-hydroxyphenyl)fluorene (BHPF) by reaction of phenol with 9-fluorenone.

The ketone starting materials may be commercial grade or better. As readily understood by one of ordinary skill in the art commercial grade reagents may contain measurable levels of typical impurities such as aldehydes, acetophenone, benzene, cumene, diacetone alcohol, water, mesityl oxide, and methanol, among others. When the ketone used is acetone it preferably contains less than about 250 ppm of methanol.

The disclosed process can also be used for the condensation of phenols with aldehydes, for example, with formaldehyde, acetaldehyde, propionaldehyde, butyraldehyde or higher homologues of the formula RCHO, wherein R is alkyl of 1–20 carbon atoms. The condensation of two moles of phenol with one mole of formaldehyde produces bis-(4-hydroxyphenyl)methane, also known as Bisphenol F.

It will be understood that dialdehydes and ketoaldehdyes, for example, glyoxal, phenylglyoxal or pyruvic aldehyde, can also be used.

The products are generally geminal bisphenols, that is, compounds having one or more single carbon atoms to which are attached nuclei of two phenolic moieties. This single carbon atom corresponds to the carbonyl carbon of the ketone or aldehyde reactant. In the case of starting materials, containing more than one aldehyde or ketone carbonyl, the product will contain more than one geminal bisphenolic moiety. For example, the condensate from acetyl acetone and phenol is 2,2,4,4-tetrakis-(hydroxyphenyl)pentane and the condensate from benzoylacetone is 2,2,4,4-tetrakis-(hydroxyphenyl)-4-phenylbutane.

Ketone is typically present in the feed in an amount sufficient to result in a phenol to ketone mole ratio greater than or equal to about 4, preferably greater than or equal to about 5, and more preferably by greater than or equal to about 7. The phenol to ketone mole ratio is typically less than or equal to about 65, preferably less than or equal to about 40, and more preferably less than or equal to about 15, based on the total weight of phenol. Ketone may be added to the phenol in a single portion (at a single location along the continuous flow through the modified ion exchange resin catalyst) or in multiple portions (multiple locations along the continuous flow through the modified ion exchange resin catalyst). Preferably the ketone is added in equal multiple portions, and most preferably in two or four equal portions along the course of the modified ion exchange resin catalyst. The ketone or aldehyde preferably contains less than or equal to about 250, more preferably less than or equal to about 225, and most preferably less than or equal to about 200 parts per million (ppm) of methanol.

There is no particular limitation with regard to the purity of the water employed in the feed. It is entirely acceptable to employ commercially available bulk water (i.e. tap water) without purification as long as the commercially available bulk water does not contain any substances that have a negative impact on the reaction to form bisphenol or on the bisphenol formed in the reaction. Alternately, if desired, distilled, deionized or distilled and deionized water may be used. The amount of water in the feed is adjusted to obtain the desired p,p bisphenol selectivity based upon the catalytic activity.

The catalytic activity of the catalyst can be ascertained on a continuous basis by determining the p,p selectivity of the reaction by determining the amount of p,p bisphenol in the effluent. In this embodiment the effluent from the reactor column is analyzed by an appropriate analytical technique such as gas chromatography, liquid chromatography or high pressure liquid chromatography for product distribution and the amount of water in the feed is adjusted to maximize the amount of the desired product in the effluent.

As can be readily appreciated by one of ordinary skill in the art, the varying amounts of water in the feed are dependent upon the identity of the catalyst, its catalytic activity and the amount of the catalyst. In another embodiment, a sample of the catalyst employed in the reactor is subjected to an accelerated lifetime test to determine the change in catalytic activity of the catalyst over time (the deactivation profile). The concentration of the water in the feed is then adjusted over time to maximize the selectivity of the reaction based on the results of the accelerated lifetime test and the amount of catalyst in the packed bed. In an accelerated lifetime test, five catalyst beds are connected in series. Feed is introduced to the first bed, the effluent from the first bed flows to the second bed, and so forth until the final effluent from the fifth bed is collected. The analysis of each bed effluent allows the monitoring of the frontal deactivation of the catalyst charge. For an accelerated lifetime test of a bisphenol catalyst, the reaction is performed under harsh conditions (high percent ketone in the feed, high temperature, very high flow rate) to ensure that the catalyst deactivation is observed.

In another embodiment, the varying amounts of water in the feed over time are determined by a design of experiment for water addition and optimization at different stages of catalyst life. A gradual change of the water level in the feed is implemented, and information on the response of the selectivity and conversion found in the reactor effluent is collected. The data is then be used to identify a feed water level that provides optimal process performance.

It is contemplated that initially the amount of water in the feed will be high, typically about 1 weight % to about 5 weight % and preferably about 1 weight % to about 2 weight % based on the total weight of the feed, as determined by Karl Fischer titration, with regular decreases depending on the p,p selectivity of the reaction. The decreases in the amount of water in the feed may be stepwise or continuous. The decreases may be determined in advance as defined by a profile (a predefined plan) or the decreases may be continuous as determined by a feedback loop which monitors the p/p reaction selectivity. Typically the decreases will be less than or equal about 0.25 weight % in size, based on the total weight of the feed, as determined by Karl Fischer titration.

The ion exchange resin comprises a cross-linked polystyrene resin that is functionalized to have acid sites. The polystyrene resin may be cross-linked with a variety of known cross-linker such as polycyclic aromatic divinyl monomers, divinyl benzene, divinyl toluene, divinyl biphenyl monomers and combinations of the foregoing cross-linkers. Preferably the polystyrene resin is cross-linked with divinylbenzene. The acid sites may comprise a sulfonic acid functionality, which upon deprotonation produces a sulfonate anion functionality, a phosphonic acid functionality, which upon deprotonation produces a phosphonate anion functionality, or a carboxylic acid functionality, which upon deprotonation produces a carboxylate anion functionality. The degree of crosslinking is typically greater than or equal to about 1%, preferably greater than or equal to about 1.5%, and more preferably greater than or equal to about 2%. Alternatively, the degree of crosslinking is less than or equal to about 8%, preferably less than or equal to about 6%, and more preferably less than or equal to about 4%. The ion exchange resin may comprise a mixture of resins with different degrees of crosslinking wherein the degree of crosslinking of each resin is as defined above.

The ion exchange resin may be a monodispersed resin, polydispersed resin, or a combination of the foregoing.

The ion exchange resin has an acidic milliequivalent per gram catalyst value (proton exchange capacity), prior to modification, of greater than or equal to about 3.5, preferably greater than or equal to about 4, and more preferably greater than or equal to about 5 meq/g when dry.

Exemplary ion exchange resin include, but are not limited to, Diaion® SK104, Diaion® SK1B, Diaion® PK208, Diaion® PK212 and Diaion® PK216 (manufactured by Mitsubishi Chemical Industries, Limited), A-121, A-232, and A-131, (manufactured by Rohm & Haas), T-38, T-66 and T-3825 (manufactured by Thermax), Lewatit K1131, Lewatit K1221 (manufactured by Bayer), Dowex® 50W2X, Dowex® 50W4X, Dowex® 50W8X resins (manufactured by Dow Chemical), Indion 180, Indion 225 (manufactured by Ion Exchange India Limited), and Purolite CT-222 and Purolite CT-122 (manufactured by Purolite).

The ion exchange resin catalyst may be used in combination with a bulk promoter or an attached promoter. Exemplary bulk promoters include, but are not limited to cylcoaliphatic thiols such as cyclohexanethiol and cyclopentanethiol, alkyl thiols such as methyl mercaptan and ethyl mercaptan, aromatic thiols such as thiophenol and benzylthiol, and aliphatic thiols such as butanethiol, hexanethiol, octadecanethiol, thioglycollic acid, and 3-mercaptopropionic acid. Bulk promoters are typically used in amount of about 200 ppm to about 2000 ppm based on weight percent SH, as determined by titration.

Exemplary attached promoters include, but are not limited to, silylmethanethiols as disclosed in U.S. Pat. No. 6,414,200, 2-mercaptomethylpyridine, cysteamine, 4-pyridylethylmercaptan, and 4-aminobutanethiol immobilized in an amine modified acidic resin catalyst, for example a sulfonated polystyrene in which about 20 percent of the sulfonic acid groups have been neutralized with pyridine. The promoter is typically fixed to an ion exchange resin support by combining the promoter with the ion exchange resin in a solvent, optionally with heat. The solvent may comprise an organic solvent such as phenol, water or a combination of an organic solvent and water. Generally the ion exchange resin is modified by neutralizing resin acid sites with the promoter or combination of promoters to form a modified ion exchange resin catalyst. In an exemplary process, the promoter(s) is combined with water to form an aqueous mixture. The aqueous mixture may further comprise an acid to improve solubility of the promoter(s). The amount of acid is sufficient to solubilize the promoter but not enough to impede modification of the ion exchange resin. Useful amounts of acid are typically less than or equal to about 1 equivalent and preferably less than or equal to about 0.25 equivalents, based on the number of moles of the promoter (s). Exemplary acids include, but are not limited to, hydrochloric acid (HCl), p-toluenesulfonic acid, trifluorocacetic acid, and acetic acid. The aqueous mixture is contacted with the ion exchange resin resulting in an ionic linkage between the promoter cation and anion (deprotonated acid site) of the ion exchange resin. Formation of the ionic linkage neutralizes the acid site.

The degree of neutralization of the ion exchange resin is greater than or equal to about 35 mole %, preferably greater than or equal to about 40 mole %, based on the total moles of acid sites. The degree of neutralization is typically less than or equal to about 75 mole %, preferably less than or equal to about 60 mole %, more preferably less than or equal to about 55 mole %, and most preferably less than or equal to about 50 mole %, based on the total moles of acid sites. The neutralization (modification) of the ion exchange resin with a promoter reduces the number of catalytic acid sites.

The degree of neutralization may be determined in a number of ways. The modified ion exchange resin catalyst may be titrated to determine the amount of remaining acid sites, the —SH content can be determined by a suitable analytical method or the nitrogen content can be determined by a suitable analytical method. The results obtained with these analytical methods are consistent with each other.

Following modification (neutralization), the modified ion exchange resin catalyst may be rinsed with a continuous flow of phenol. Alternatively, if acid was used to improve the solubility of the promoter, the modified ion exchange resin is typically rinsed with deionized water prior to rinsing with phenol. Preferably the phenol has been subjected to purification steps to remove metallic and organic impurities that may be present through the use of resin treatment as taught in U.S. Pat. No. 5,414,151 or other known purification methods.

The feed may also contain low levels of bisphenol and impurities resulting from the manufacture of bisphenol. As described below, it can be desirable to recycle residual phenol and other starting materials found in the effluent stream. The residual phenol and other starting materials are typically isolated before being recycled to the reaction feed but small amounts of impurities can remain and thus become part of the feed. Typically, the amount of bisphenol and other materials that are not reaction starting materials is less than about 2% by weight, based on the total weight of the feed and as determined by liquid chromatography (LC) although it is contemplated that the amount of bisphenol and other non-reaction starting materials present in the feed may be in amounts as high as about 25% by weight, based on the total weight of the feed and as determined by liquid chromatograph (LC).

The feed comprising phenol, ketone and water is passed through the modified ion exchange resin catalyst at an overall weight hourly space velocity greater than or equal to about 0.1, preferably greater than or equal to about 0.5, and more preferably greater than or equal to about 0.6. The feed comprising phenol and ketone is typically passed through the modified ion exchange resin catalyst at an overall weight hourly space velocity less than or equal to about 10.0, preferably less than or equal to about 8.0, and more preferably less than or equal to about 3.0, and more preferably less than or equal to about 2.5.

The feed comprising phenol, ketone and water is introduced to the modified ion exchange resin catalyst at a temperature above the freezing point of the feed, typically about 10° C. to about 100° C. Within this range the introductory temperature is preferably greater than or equal to about 30° C., preferably greater than or equal to about 40° C., more preferably greater than or equal to about 45° C. Also within the above mentioned range, the temperature of the modified ion exchange resin catalyst at the introduction of the feed is less than or equal to about 90° C., and preferably less than or equal to about 80° C.

Passing the feed through the modified ion exchange resin catalyst results in an effluent comprising bisphenol, residual starting materials, water produced in the reaction, and side products. The bisphenol produced (in the reaction) is predominantly para—para (p/p)bisphenol although some ortho-para (o/p) is produced. Typically the average ratio of p/p:o/p is greater than or equal to about 20, preferably greater than or equal to about 30 and more preferably greater than or equal to about 40. The effluent contains greater than or equal to about 10%, preferably greater than or equal to about 12%, and more preferably greater than or equal to about 15% by weight total bisphenol (o/p and p/p combined), based on the total weight of the effluent.

The bisphenol may then be isolated from the residual starting materials, water and side products found in the effluent. In the isolation process, water, residual ketone and optionally some residual phenol are removed first, typically by vacuum distillation resulting in a bisphenol containing product stream. The removed ketone and residual phenol can be separated from the water and recycled to the reaction feed. The p/p bisphenol may be isolated from the bisphenol containing product stream by adduct crystallization, solvent crystallization, melt crystallization, distillation, or a combination of the foregoing isolation methods. If adduct crystallization is employed in combination with any of the other isolation methods, it is preferable for adduct crystallization to comprise the first step and the other isolation method(s) to comprise the subsequent step(s) of the chosen combination. The phenol removed from the product stream may be recycled for use in the catalyzed reaction or adduct crystallization when present. Advantageously, the high degree of selectivity of the reaction for p/p bisphenol results in the amount of impurities being greatly reduced, thus facilitating the isolation of the p/p bisphenol, improving the overall efficiency of the reaction and isolation, lengthening the life of the catalyst, as well as reducing the cost of the production of p/p bisphenol. The ability of this process to be used with a virgin feed system, without significant recycle of impurities to the reactor, also results in a higher purity effluent, further simplifying or eliminating the purification process.

The bisphenol may be used in the synthesis of polycarbonate. Polycarbonate may be synthesized by interfacial polymerization methods or by transesterification methods. In interfacial polymerization, an aqueous solution of a bisphenol is combined with an organic solution containing an organic solvent and a carbonic acid derivative, such as carbonyl halides, diaryl carbonate esters and haloformates such as phosgene, in the presence of a polymerization catalyst. Polymerization occurs at the interface between two phases. Additionally a monofunctional compound such as a phenol, tert-butyl phenol or para-cumylphenol, may be present to function as a chain termination agent to limit the molecular weight of the polycarbonate. A polyfunctional compound, herein defined as having more than two functional groups, may also be present to function as a branching agent. An exemplary polyfunctional compound is tris-hydroxyphenolethane (THPE).

Useful organic solvents include, but are not limited to, aliphatic hydrocarbons, chlorinated aliphatic hydrocarbons, aromatic hydrocarbons, substituted aromatic hydrocarbons and carbon disulfide. The chlorinated aliphatic hydrocarbons, especially methylene chloride, are preferred.

Exemplary polymerization catalysts include tertiary amines, typically a trialkylamine such as triethylamine, highly nucleophilic heterocyclic amines such as 4-dimethylaminomorpholine, phase transfer catalysts such as quaternary ammonium salts and mixtures of the foregoing. Exemplary quaternary ammonium salts include tetra-t-butylammonium chloride or bromide and tetra-t-butylphosphonium chloride or bromide.

Transesterification may be performed with or without solvent. When performed without solvent the reaction is run at high temperature and low pressure and has come to be known as "melt polymerization." In transesterification, a carbonate diester is condensed with bisphenol in the presence of a polymerization catalyst such as the amines described above, guanidine, alkali metal phosphates, and alkali earth metal phosphates. The reaction mixture may further comprise a polyfunctional compound and/or a monofunctional compound as described above.

Figure 3:
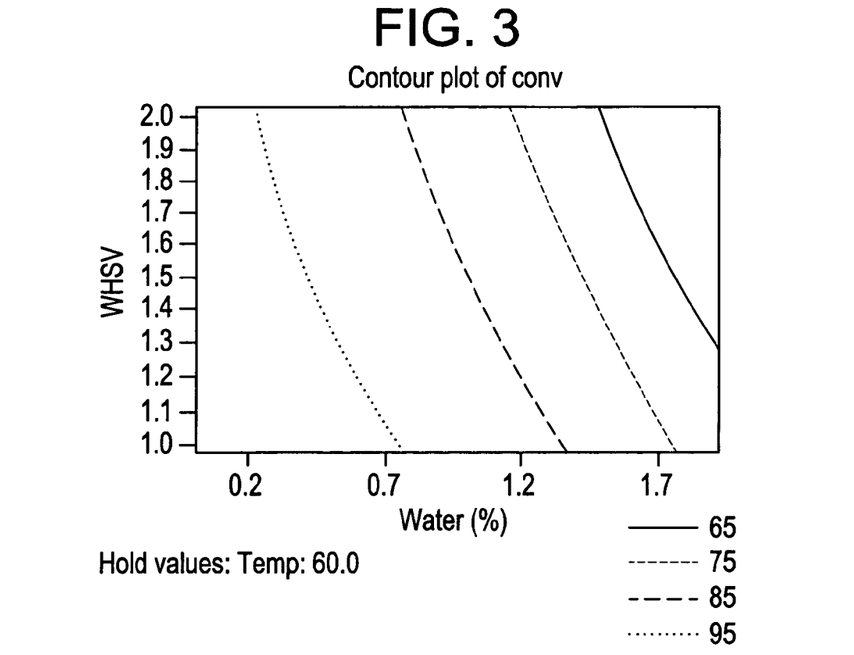
FIG. 3 is a contour plot of acetone conversion.

Useful carbonate diesters include, but are not limited to, diphenyl carbonate, bis(4-t-butylphenyl)carbonate, bis(2,4-dichlorophenyl)carbonate, bis methyl salicyl carbonate, bis (2,4,6-trichlorophenyl)carbonate, bis(2-cyanophenyl) carbonate, bis(o-nitrophenyl)carbonate, ditolyl carbonate, m-cresol carbonate, dinapthyl carbonate, bis(diphenyl)carbonate, diethyl carbonate, dimethyl carbonate, dibutyl carbonate, or dicylcohexyl carbonate. Of these, diphenyl carbonate is preferred. If two or more of these compounds is combined, it is preferable to use diphenyl carbonate as one component of the combination FIG. 3 demonstrates the dependence of conversion on WHSV and added water. The conversion is decreased by increased space velocity or added water (or both). This illustrates how the addition of water mimics an actual change in the space velocity. The decrease in conversion is coincident with a decreasing isomerization zone in the reactor bed.

Figure 4:
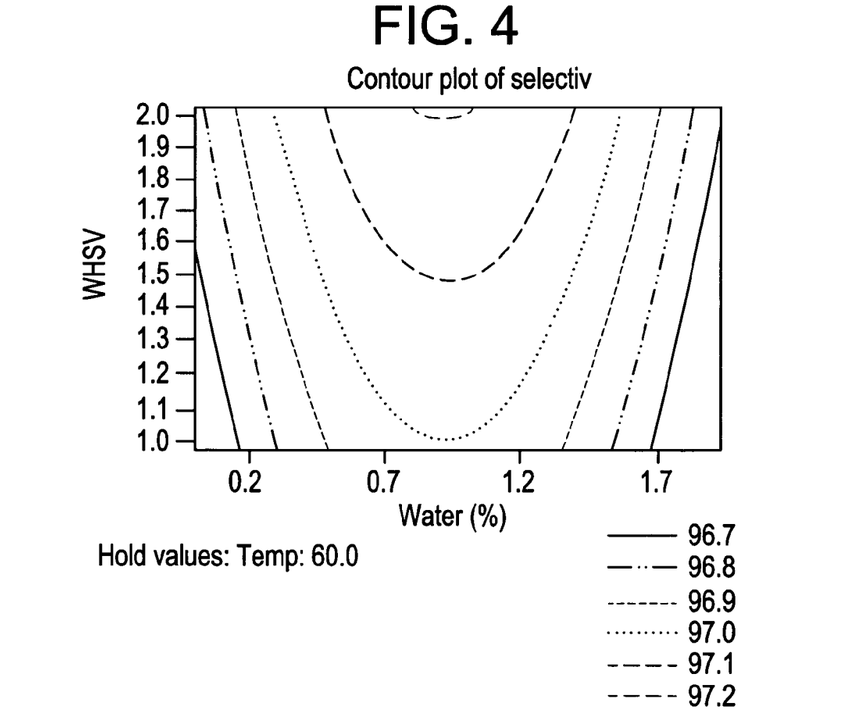
FIG. 4 is a contour plot of reaction selectivity.

FIG. 4 illustrates the dependence of selectivity on WHSV and added water. Increasing WHSV results in an increase in selectivity.

All cited patents are incorporated herein by reference in their entirety.

The invention is further illustrated by the following non-limiting examples.

EXAMPLES

Comparative Example 1

Figure 1:
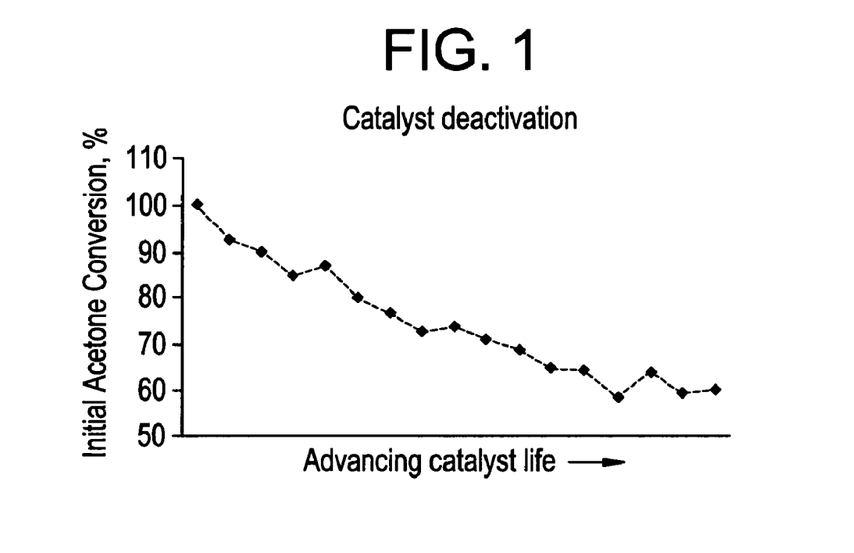
FIG. 1 is a graphical illustration of catalyst deactivation.

A feed containing 94 weight percent (wt %)phenol and 6 wt % acetone based on the total weight of the feed was fed continuously to a series of five reactor beds, each containing 1.25 grams of a acidic 2% crosslinked ion exchange resin; which had been treated with a mercaptoamine such that 30% (eq/eq) of the sulfonic acid sites were neutralized with the mercaptoamine. As can be seen in FIG. 1, the initial catalyst activity in the first reactor bed was high and declined as the catalyst became deactivated. The drop in acetone conversion (and therefore p,p-bisphenol production) resulted in a changing composition of the reactor effluent.

Example 1

Figure 2:
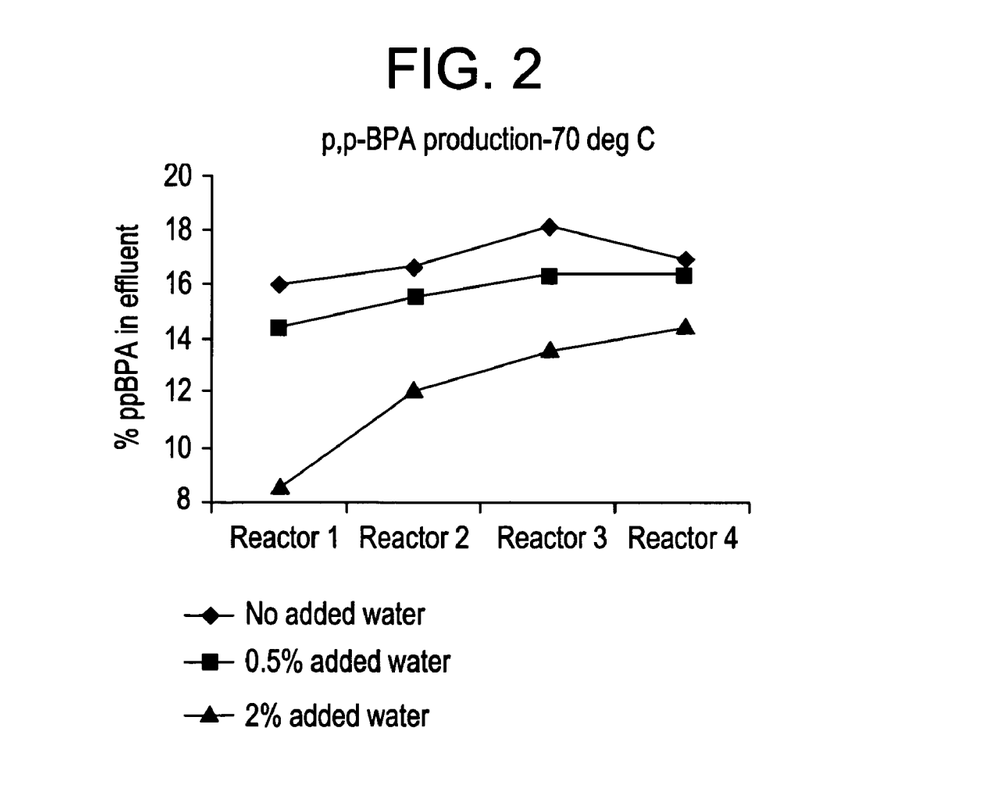
FIG. 2 is a graphical illustration of the effect of water in the feed.

A feed containing 5 weight % acetone, the indicated amount of water, and the balance phenol based on weight was fed continuously to a 4 columns arranged in series, each containing 10 g of fresh 2% crosslinked Rohm and Haas ion exchange catalyst, with 37% of its acid sites modified with 4-pyridylethylmercaptan. The bis-phenol A production through a catalyst bed was tracked and the results are shown in FIG. 2. One can see that, without water present, the maximum amount of p,p-BPA was actually reached in the third stage of the catalyst bed. Therefore, the fourth stage merely acted as an isomerization catalyst, reducing the purity of the reactor effluent and the selectivity of the overall reaction.

Examples 2–7

Four columns, each containing 10 grams of ion exchange catalyst having 2% crosslinking (available from Rohm and Haas) and 37% of its acid sites modified with 4-pyridylethylmercaptan were arranged in series. The columns were surrounded by water jackets maintained at a temperature of about 60° C. (Examples 1–3) or 70° C. (Examples 5–7). The feed to the columns consisted of water, phenol and 5% by weight of acetone. Addition of the feed to each column was controlled by a pump so as to attain an overall space velocity of 1 WHSV. The effluent from the each column was sampled and analyzed by acetone titration, and liquid chromatography. Selectivity is defined as the weight percent of p,p-bisphenol (for p,p-bisphenol selectivity) or the combined weight percent of p,p-bisphenol and o,p-bisphenol (for overall bisphenol selectivity) divided by the combined weight percent of all reaction products. Results are shown in Table 1.

TABLE 1

|  | 2 | 3 | 4 | 5 | 6 | 7 |
| --- | --- | --- | --- | --- | --- | --- |
| Concentration of water in feed | 653 ppm | 5246 ppm | 1.866% | 455 ppm | 5044 ppm | 1.844% |
| Weight percent of p,p-bisphenol in effluent | 17.1% | 16.7% | 12.9% | 16.9% | 16.4% | 14.6% |

TABLE 1-continued

|  | 2 | 3 | 4 | 5 | 6 | 7 |
|---|---|---|---|---|---|---|
| p,p-bisphenol selectivity | 96.71% | 96.91% | 96.59% | 95.14% | 96.10% | 95.95% |
| Overall bisphenol Selectivity | 98.75% | 98.74% | 98.72% | 98.31% | 98.85% | 98.77% |
| p,p/o,p ratio | 47.2 | 53.1 | 45.4 | 30.0 | 34.9 | 34.1 |
| Overall Conversion | 99.5% | 97.8% | 71.5% | 99.7% | 99.5% | 83.2% |

Examples 2–7 demonstrate that the addition of the appropriate amount of water results in an improvement in p,p-bisphenol selectivity.

Examples 8–9

Four columns, each containing 10 grams of ion exchange catalyst having 2% crosslinking (available from Rohm and Haas) and 33% of its acid sites modified with 4-pyridylethylmercaptan were arranged in series. The columns were surrounded by water jackets maintained at a temperature of about 55° C. The feed to the columns consisted of water, phenol and 1.25% by weight of acetone. Addition of the feed to each column was controlled by a pump so as to attain an overall space velocity of 2 WHSV. An additional 1.25% by weight of acetone was injected continuously into the process before stages 2, 3, and 4 for a total acetone charge of 5% by weight over all four columns. The effluent from the each column was sampled and analyzed by acetone titration, and liquid chromatography. Selectivity is defined as the weight percent of p,p-bisphenol (for p,p-bisphenol selectivity) or the combined weight percent of p,p-bisphenol and o,p-bisphenol (for overall bisphenol selectivity) divided by the combined weight percent of all reaction products. Results are shown in Table 2.

TABLE 2

|  | 8 | 9 |
|---|---|---|
| Concentration of water in feed | 319 ppm | 1078 ppm |
| % p,p-BPA in effluent | 14.9% | 15.1% |
| P,p-BPA Selectivity | 97.41% | 97.49% |
| Overall BPA Selectivity | 99.03% | 99.02% |
| Pp/op ratio | 60.3 | 62.3 |
| Overall Conversion | 87.3% | 83.5% |

Example 10

A feed containing 5 weight % acetone, 0.2 weight % water, and the balance phenol based on weight is fed continuously to 4 columns arranged in series, each containing 10 g of fresh 2% crosslinked Rohm and Haas ion exchange catalyst, with 37% of its acid sites modified with 4-pyridylethylmercaptan. The reaction has a flow rate of WHSV=2 hr$^{-1}$. The conversion is 95.95% and the selectivity is 96.93%. When process conditions in the plant change, and require that the flow rate be cut in half, the WHSV drops to 1 hr$^{-1}$ and the conversion increases to 99.8%, while the selectivity drops to 96.72%. The amount of water in the feed is then increased to 0.7 weight %. With the increase of water content in the feed, the conversion is 95.95% and the selectivity is 96.97%. When the flow rate through the reactor is returned to the original flow rate, the water concentration is decreased to 0.2 weight % resulting in a conversion of 95.95% and a selectivity of 96.93%. Conversion is maintained at a constant level and selectivity is maintained at a nearly constant level through the adaptation of the water content in the feed based on flow rate.

As can be seen from the foregoing Examples, it is possible to produce bisphenol to improve p,p selectivity by utilizing water in the reactor feed.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A continuous process for the reaction of a ketone or an aldehyde with a phenol to form a bisphenol comprising reacting a feed comprising a phenol, water and a ketone or aldehyde in the presence of an ion exchange resin catalyst to produce an effluent; determining the para—para bisphenol selectivity of the reaction; and adjusting the concentration of the water in the feed based upon the para—para bisphenol selectivity.

2. The process of claim 1, wherein said ketone is acetone and said phenol is a hydroxy aromatic compound with at least one unsubstituted position.

3. The process of claim 2 wherein the unsubstituted position is para to the hydroxy position.

4. The process of claim 2 wherein the phenol is substituted with at least one inert substituent.

5. The process of claim 1, wherein the phenol to ketone mole ratio is about 4 to about 65.

6. The process of claim 1, wherein said phenol is selected from the group consisting of phenol, 2-cresol, 3-cresol, 2,6-dimethylphenol, resorcinol, napthol and mixtures of two or more of the foregoing phenols.

7. The process of claim 1, wherein said ketone is selected from the group consisting of 9-fluorenone, benzophenone, acetone, acetophenone, cyclohexanone, 3,3,5-trimethylcyclohexanone, 4-hydroxyacetophenone, 4,4'-dihydroxybenzophenone and mixtures of two or more of the foregoing ketones.

8. The process of claim 1, wherein said aldehyde is selected from the group consisting of formaldehyde, acetaldehyde, propionaldehyde, butyraldehyde and mixtures of two or more of the foregoing aldehydes.

9. The process of claim 1, wherein the reaction has a weight hour space velocity of about 0.1 to about 10.

10. The process of claim 1, wherein the feed has a temperature of about 40 to about 90° C.

11. The process of claim 1, wherein the para/para selectivity of the reaction is greater than about 94%.

12. The process of claim 1, wherein the catalyst has a degree of crosslinking of about 1.5% to about 6.0%.

13. The process of claim 12, wherein catalyst is a mixture of resins of different degrees of crosslinking wherein the degree of crosslinking of each resin comprising the mixture is about 1.5 to about 6%.

14. The process of claim 1 wherein the catalyst has a degree of neutralization of about 35 to about 60 mole %.

15. The process of claim 1, wherein the process has a conversion level greater than or equal to about 70%.

16. The process of claim 1, wherein the amount of water in the feed is less than or equal to about 5 weight percent, based on the total weight of the feed.

17. The process of claim 1, wherein the catalyst further comprises an attached promoter.

18. The process of claim 17, wherein the attached promoter is cysteamine, 4-pyridylethylmercaptan or a combination of the foregoing.

19. The process of claim 1, wherein the ketone or aldehyde is added in a single portion.

20. The process of claim 1, wherein the ketone or aldehyde is added in multiple portions.

21. The process of claim 1, wherein the feed comprises recycled compounds.

22. The process of claim 1, wherein the catalyst further comprises a bulk promoter.

23. A process for the manufacture of polycarbonate comprising continuously reacting a feed comprising a phenol, a ketone and water in the presence of an ion exchange resin catalyst to produce an effluent comprising bisphenol; determining the para—para bisphenol selectivity of the reaction; adjusting the concentration of the water in the feed based upon the para—para bisphenol selectivity; and reacting said bisphenol with a carbonic acid derivative or a carbonate diester in the presence of a polymerization catalyst.

24. A continuous process for the reaction of a ketone with a phenol to form a bisphenol in the presence of a catalyst comprising determining the catalytic activity of the catalyst over time; introducing a feed comprising water; phenol and ketone to the catalyst; reacting the phenol and ketone in the presence of the catalyst; controlling the concentration of the water in the feed based upon the amount of catalyst and catalytic activity; wherein the reaction has a para—para bisphenol selectivity of at least about 94%.

25. A process for the manufacture of polycarbonate comprising continuously synthesizing a bisphenol in the presence of a catalyst by determining the catalytic activity of the catalyst; introducing a feed comprising water, phenol and ketone to the catalyst; reacting the phenol and ketone in the presence of the catalyst to form bisphenol; controlling the concentration of the water in the feed based upon the amount of catalyst and catalytic activity; and reacting the bisphenol with a carbonic acid derivative or a carbonic diester in the presence of a polymerization catalyst, wherein the reaction generating bisphenol has a para—para bisphenol selectivity of at least about 94%.

26. A continuous process for the reaction of a ketone with a phenol to form a bisphenol comprising reacting a feed comprising a phenol, a ketone and a first concentration of water in the presence of an ion exchange resin catalyst at a first flow rate to produce an effluent; and reacting a feed comprising a phenol, a ketone and a second concentration of water in the presence of the ion exchange resin catalyst at a second flow rate to produce an effluent, wherein the reaction at the first flow rate has a para—para bisphenol selectivity within about 1% of the para—para bisphenol selectivity of the reaction at the second flow rate and the first concentration of water does not equal the second concentration of water.

* * * * *